(12) United States Patent
Al-Shammari

(10) Patent No.: US 12,233,405 B2
(45) Date of Patent: Feb. 25, 2025

(54) HEATING PLATES RISER REACTOR

(71) Applicant: SABIC Global Technologies B.V., Bergen op Zoom (NL)

(72) Inventor: Talal Khaled Al-Shammari, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 293 days.

(21) Appl. No.: 17/630,459

(22) PCT Filed: Jul. 14, 2020

(86) PCT No.: PCT/IB2020/056616
§ 371 (c)(1),
(2) Date: Jan. 26, 2022

(87) PCT Pub. No.: WO2021/019345
PCT Pub. Date: Feb. 4, 2021

(65) Prior Publication Data
US 2022/0250022 A1    Aug. 11, 2022

Related U.S. Application Data

(60) Provisional application No. 62/881,232, filed on Jul. 31, 2019.

(51) Int. Cl.
*B01J 8/18* (2006.01)
*B01J 8/26* (2006.01)
(Continued)

(52) U.S. Cl.
CPC ........... *B01J 8/1836* (2013.01); *B01J 8/1872* (2013.01); *B01J 8/26* (2013.01); *B01J 8/388* (2013.01);
(Continued)

(58) Field of Classification Search
None
See application file for complete search history.

(56) References Cited

U.S. PATENT DOCUMENTS 2,994,659 A    8/1961    Slyngstad et al.
3,142,542 A    7/1964    Schwarzenbek et al.
(Continued)

FOREIGN PATENT DOCUMENTS

CA    1205034 A    5/1986
CN    101314724 A    12/2008
(Continued)

OTHER PUBLICATIONS

Garcia-Dopico et al. "Modelling fluidized catalytic cracking unit stripper efficiency." *Chem. Ind. Chem. Eng. Q.* 21 (1) 95-105 (2015).
(Continued)

*Primary Examiner* — Ali Z Fadhel
(74) *Attorney, Agent, or Firm* — Norton Rose Fulbright US LLP

(57) ABSTRACT

A system and a method for catalytically cracking hydrocarbons. The system includes a fluidized bed riser reactor, and a separation zone configured to separate the effluent from the riser reactor to produce a product stream and a spent catalyst. A stripping zone is fluidly coupled to the outlet of the separation zone such that the spent catalyst is stripped to remove the hydrocarbons adsorbed thereon. The stripping zone encompasses at least a portion of the riser reactor such that stripping internals in the stripping zone are used to provide reaction heat to the riser reactor.

19 Claims, 2 Drawing Sheets

(51) Int. Cl.
  *B01J 8/38* (2006.01)
  *C07C 4/00* (2006.01)
  *C10G 11/18* (2006.01)
(52) U.S. Cl.
  CPC .............. *C10G 11/182* (2013.01); *C07C 4/00* (2013.01); *C10G 2300/4093* (2013.01); *C10G 2400/20* (2013.01); *C10G 2400/30* (2013.01)

(56) References Cited

U.S. PATENT DOCUMENTS

| | | | |
|---|---|---|---|
| 3,690,841 | A | 9/1972 | Bunn, Jr. et al. |
| 4,356,082 | A * | 10/1982 | Gross .................... C10G 11/18 208/159 |
| 4,605,491 | A | 8/1986 | Haddad et al. |
| 4,721,603 | A | 1/1988 | Krug et al. |
| 4,946,656 | A | 8/1990 | Ross et al. |
| 4,971,681 | A | 11/1990 | Harandi et al. |
| 4,973,398 | A | 11/1990 | Pappal et al. |
| 4,990,314 | A | 2/1991 | Herbst et al. |
| 5,062,945 | A | 11/1991 | Pappal et al. |
| 5,141,625 | A | 8/1992 | Lomas |
| 5,380,426 | A | 1/1995 | Johnson et al. |
| 6,027,696 | A | 2/2000 | Das et al. |
| 8,685,232 | B2 | 4/2014 | Mandal et al. |
| 2003/0211017 | A1 | 11/2003 | Pankaj et al. |
| 2005/0029163 | A1 * | 2/2005 | Letzsch ................ C10G 11/187 208/159 |
| 2011/0240523 | A1 | 10/2011 | Mandal et al. |
| 2016/0168050 | A1 | 6/2016 | Fei et al. |

FOREIGN PATENT DOCUMENTS

| | | |
|---|---|---|
| CN | 101362959 A | 2/2009 |
| CN | 101362964 A | 2/2009 |
| CN | 102292417 A | 12/2011 |
| CN | 103059923 A | 4/2013 |
| CN | 103509594 A | 1/2014 |
| CN | 105505456 B | 9/2017 |
| CN | 109833834 A | 6/2019 |
| WO | WO90/09842 A1 | 9/1990 |

OTHER PUBLICATIONS

International Search Report and Written Opinion from PCT/IB2020/056616 dated Sep. 16, 2020, 13 pages.

* cited by examiner

HEATING PLATES RISER REACTOR

CROSS REFERENCE TO RELATED APPLICATIONS

This application is a national phase application under 35 U.S.C. § 371 of International Application No. PCT/IB2020/056616 filed Jul. 14, 2020, which claims priority to U.S. Provisional Patent Application No. 62/881,232 filed Jul. 31, 2019. The entire contents of each of the above-referenced disclosures is specifically incorporated by reference herein without disclaimer.

FIELD OF INVENTION

The present invention generally relates to systems and methods for catalytically cracking hydrocarbons. More specifically, the present invention relates to hydrocarbon catalytic cracking systems and methods that includes heating plates in a catalyst stripping zone configured to provide heat to a catalytic cracking riser.

BACKGROUND OF THE INVENTION

Light olefins ($C_2$ to $C_4$ olefins) are building blocks for many chemical processes. Light olefins are used to produce polyethylene, polypropylene, ethylene oxide, ethylene chloride, propylene oxide, and acrylic acid, which, in turn, are used in a wide variety of industries such as the plastic processing, construction, textile, and automotive industries. Generally, light olefins are produced by steam cracking naphtha and dehydrogenating paraffin.

BTX (benzene, toluene, and xylene) are a group aromatics that are used in many different areas of the chemical industry, especially the plastic and polymer sectors. For instance, benzene is a precursor for producing polystyrene, phenolic resins, polycarbonate, and nylon. Toluene is used for producing polyurethane and as a gasoline component. Xylene is feedstock for producing polyester fibers and phthalic anhydride. In the petrochemical industry, benzene, toluene, and xylene are conventionally produced by catalytic reforming of naphtha.

Over the last few decades, the demands for light olefins and BTX have been consistently increasing. Other methods, including catalytic cracking of naphtha, have been explored to produce light olefins and/or BTX to meet the demands. However, the catalytic cracking of hydrocarbons is highly endothermic. Thus, it is challenging to prevent temperature drop in the catalytic cracker during the catalytic cracking process. Simply increasing the temperature in the catalytic cracking reactor may be able to provide enough reaction heat, but high reaction temperature can reduce the catalyst stability and catalyst life, resulting in increased production cost. Furthermore, conventional catalytic cracking systems are generally configured to have a low hydrocarbon-catalyst contact time, resulting in low coke formation on the catalyst. This can be problematic as the low coke content on the catalyst can lead to insufficiently heated regenerated catalyst being fed back to the catalytic cracking reactor. Lack of reaction heat in the catalytic cracking reactor can cause low reaction rate, low selectivity to light olefins and BTX, thereby increasing production cost for light olefins and BTX.

Overall, while systems and methods of producing light olefins and BTX via catalytic cracking exist, the need for improvements in this field persists in light of at least the aforementioned drawbacks for the methods.

BRIEF SUMMARY OF THE INVENTION

A solution to at least some of the above-mentioned problems associated with the systems and methods for catalytic cracking hydrocarbons has been discovered. The solution resides in a system for catalytic cracking hydrocarbons that includes a catalyst stripping zone encompassing at least a portion of a catalytic cracking riser and configured to provide heat to the catalytic cracking riser. This can be beneficial in compensating for the insufficient heating of regenerated catalyst and temperature drop in the catalytic cracking riser caused by the highly endothermic cracking reaction. Additionally, the stripping medium (gas) used for stripping spent catalyst can be used as a heating medium, thereby eliminating the need for adding extra heating medium. Furthermore, the flue gas produced during the catalyst regeneration step can be used to heat the internals of stripping zone and/or the heating medium, thereby saving energy for providing reaction heat in the catalytic cracking riser. Therefore, the method of the present invention provides a technical solution to at least some of the problems associated with the conventional systems and methods for catalytically cracking hydrocarbons.

Embodiments of the invention include a fluidized catalytic cracking apparatus. The apparatus comprises a reaction riser configured to receive a mixture comprising a hydrocarbon feed and a cracking catalyst and to crack the hydrocarbon feed to produce cracked hydrocarbons and a spent catalyst comprising hydrocarbons adsorbed thereto. The apparatus comprises a stripping zone fluidly coupled to the reaction riser and encompassing at least a portion of the reaction riser. The stripping zone is configured to receive the spent catalyst comprising hydrocarbons adsorbed thereto from the riser. The stripping zone comprises a stripping medium inlet configured to receive a stripping medium. The stripping zone comprises a plurality of internals configured to (a) strip the hydrocarbons adsorbed thereto from the spent catalyst via the stripping medium and/or (b) provide heat to the reaction riser.

Embodiments of the invention include a fluidized catalytic cracking apparatus. The apparatus comprises a reaction riser configured to receive a mixture comprising a heavy hydrocarbon feed and a cracking catalyst and crack the hydrocarbons to produce cracked hydrocarbons and a spent catalyst comprising hydrocarbons adsorbed thereto. The apparatus comprises a stripping zone fluidly coupled to the reaction riser and encompassing at least a portion of the reaction riser. The stripping zone is configured to receive the spent catalyst comprising hydrocarbons adsorbed thereto from the riser. The stripping zone comprises a stripping medium inlet configured to receive a stripping medium. The apparatus further comprises an outlet fluidly coupled to the stripping zone, configured to release stripped spent catalyst from the stripping zone. The apparatus further still comprises a catalyst regenerator fluidly coupled to the outlet. The catalyst regenerator is configured to regenerate the stripped spent catalyst to produce flue gas and a regenerated catalyst. The apparatus further still comprises separation zone fluidly coupled to the stripping zone and encompassing at least a portion of the reaction riser. The separation zone comprises a cyclone system fluidly coupled to an outlet of the reaction riser, and configured to separate an effluent stream from the reaction riser to form a product stream and the spent catalyst. The separation zone comprises a reactor shell encompassing the cyclone system and the spent catalyst released from the cyclone system.

Embodiments of the invention include a method of catalytically cracking hydrocarbons. The method comprises feeding a hydrocarbon stream comprising hydrocarbons and a catalyst into a reaction riser of the fluidized catalytic cracking apparatus. The method comprises subjecting, in the reaction riser, the hydrocarbon stream under reaction conditions sufficient to crack the hydrocarbons and produce an effluent stream comprising cracked hydrocarbons, unreacted hydrocarbons, and a spent catalyst. The method comprises supplying heat from the stripping zone to the reaction riser to maintain a reaction temperature in the reaction riser. The method comprises separating, in the separation zone, the effluent stream to produce a product stream comprising the cracked hydrocarbons and/or unreacted hydrocarbons, and a spent catalyst stream comprising the spent catalyst. The method further comprises stripping, in the stripping zone, the spent catalyst to produce a stripped catalyst by the stripping medium. The method further still comprises regenerating, in a catalyst regenerator, the spent catalyst to produce a regenerated catalyst and flue gas.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, the catalytic cracking systems for producing light olefins and BTX suffer several drawbacks that limit the production efficiency and increase the production for light olefins and BTX. First of all, the temperature drop in the reaction riser caused by the highly endothermic cracking reaction can reduce the production efficiency for light olefins and BTX. Simply increasing the temperature of the catalyst can address the temperature drop, but it can also reduce the catalyst stability and catalyst life, resulting in increased production cost. Secondly, due to low coke formation on the surface of the catalyst during the catalytic cracking process, the regeneration of the catalyst may not be able to sufficiently restore heat to the catalyst for the cracking process. Increasing catalyst to oil ratio in the reaction riser may be able to address this issue, but the high cost of the catalyst can increase the production cost of light olefins and BTX. The present invention provides a solution to at least some of these problems. The solution is premised on a system and a method for catalytic cracking hydrocarbons that include using internals in a catalyst stripping zone to provide heat to the reaction riser, thereby mitigating the temperature drop in the reaction riser. Additionally, the stripping medium can be used as the heating medium for heating the reaction riser, eliminating the need to introduce additional heating medium. Moreover, the flue gas produced in the catalyst regeneration process can be used to generate heat for the internals in the stripping zone and/or the stripping medium, thereby reducing the cost for providing the reaction heat. These and other non-limiting aspects of the present invention are discussed in further detail in the following sections.

A. Systems for Catalytic Cracking

Figure 1:
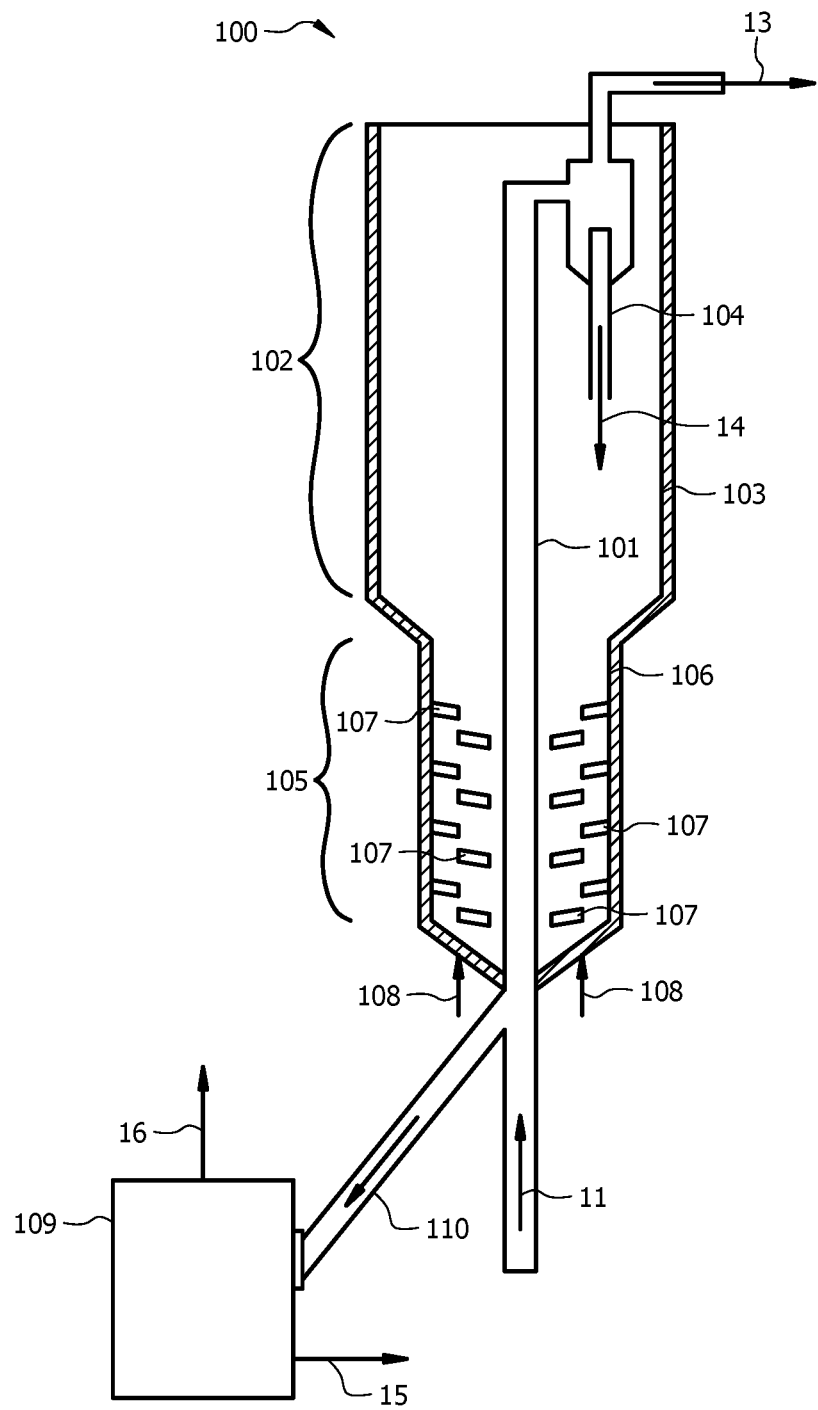
FIG. 1 shows a schematic diagram of a system for catalytic cracking hydrocarbons, according to embodiments of the invention.

In embodiments of the invention, a system for catalytic cracking hydrocarbons can include a reaction riser, a separation zone, a stripping zone, and a catalyst regenerator. With reference to FIG. 1, a schematic diagram is shown of system 100 that is configured to provide supplement reaction heat to the catalytic cracking process with low cost. According to embodiments of the invention, system 100 includes reaction riser 101. In embodiments of the invention, reaction riser 101 can be a fluidized bed riser reactor configured to receive feed stream 11.

According to embodiments of the invention, feed stream 11 comprises a catalyst and a hydrocarbon mixture. The hydrocarbon mixture may include full range naphtha, light naphtha, or heavy naphtha. Feed stream 11 may have a catalyst to oil ratio (weight based) in a range of 3 to 30 and all ranges and values there between including ranges of 3 to 6, 6 to 9, 9 to 12, 12 to 15, 15 to 18, 18 to 21, 21 to 24, 24 to 27, and 27 to 30. In embodiments of the invention, reaction riser 101 is configured to catalytically crack hydrocarbons (e.g., full range naphtha, light naphtha, or heavy naphtha) of stream 11 in the presence of the catalyst to produce an effluent stream (not shown in FIG. 1) comprising (1) cracked hydrocarbons including light olefins and/or BTX and (2) a spent catalyst. The spent catalyst can include coke formed thereon and/or residual hydrocarbons adsorbed thereto. Non-limiting examples of the catalyst may include ZSM-5, SAPO-34, dual function catalysts, or combinations thereof. The catalyst may have an average particle size of 70 to 150 μm and all ranges and values there between including ranges of 70 to 80 μm, 80 to 90 μm, 90 to 100 μm, 100 to 110 μm, 110 to 120 μm, 120 to 130 μm, 130 to 140 μm, and 140 to 150 μm.

According to embodiments of the invention, system 100 includes separation zone 102 configured to separate the effluent stream to produce product stream 13 comprising the cracked hydrocarbons and spent catalyst stream 14 comprising the spent catalyst. In embodiments of the invention, separation zone 102 comprises (1) cyclone system 104 including one or more cyclone separators and (2) separation shell 103 encompassing cyclone system 104. Separation shell 103 may encompass at least a portion of reaction riser 101. In embodiments of the invention, an outlet of reaction riser 101 is in fluid communication with the one or more cyclone separators such that the effluent stream from reaction riser 101 flows to cyclone system 104.

According to embodiments of the invention, a bottom outlet of separation shell 103 is in fluid communication with stripping zone 105 such that spent catalyst stream 14 flows from separation shell 103 to stripping zone 105. In embodiments of the invention, stripping zone 105 is configured to strip hydrocarbons adsorbed on spent catalyst using a stripping medium. Non-limiting example for the stripping medium can include steam, air, dry gas, and combinations thereof. Stripping zone 105 may comprise stripping shell 106 encompassing at least a portion of reaction riser 101 and internals 107 configured to strip the spent catalyst and provide heat to reaction riser 101. Stripping zone 105 may further comprise one or more stripping medium inlets 108 configured to receive the stripping medium into stripping shell 106. In embodiments of the invention, non-limiting example of internals 107 may include heating plates, heating coils, or combinations thereof. Internals 107, in embodiments of the invention, may be configured to heat the stripping medium, which provides heat to reaction riser 101. As an alternative or in addition to heating the stripping medium, internals 107 may be configured to directly heat reaction riser 101. Heating plates may be coupled to a wall of stripping shell 106 and/or submerged in stripping zone 105.

According to embodiments of the invention, an outlet of stripping zone 106 is in fluid communication with catalyst regenerator 109 via spent catalyst standpipe 110 such that stripped spent catalyst is transported from stripping zone 105 to catalyst regenerator 109. In embodiments of the invention, catalyst regenerator 109 is configured to regenerate stripped spent catalyst to produce (1) regenerated catalyst stream 15 comprising regenerated catalyst and (2) flue gas stream 16 comprising flue gas. In embodiments of the invention, flue gas stream 16 may be used to produce heat for internals 107. Flue gas stream 16 may be used to heat the stripping medium. In embodiments of the invention, flue gas stream 16 comprises steam, air, dry gas, or combinations thereof. In embodiments of the invention, the flue gas may be used as a stripping medium in stripping zone 105. According to embodiments of the invention, regenerated catalyst stream 15 is fed to reaction riser 101 with the hydrocarbon mixture.

B. Method of Catalytic Cracking Hydrocarbons

Figure 2:
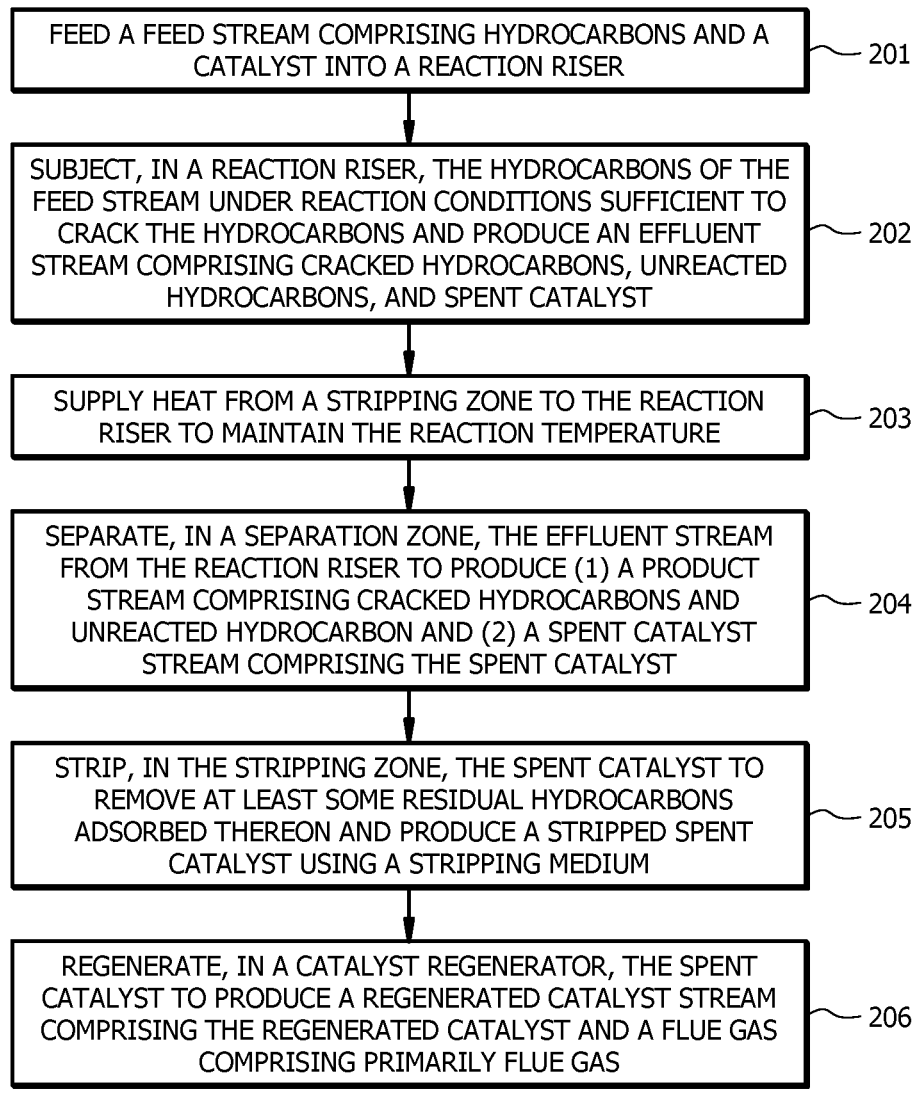
FIG. 2 shows a schematic flowchart of a method for catalytic cracking hydrocarbons, according to embodiments of the invention.

Methods of catalytic cracking hydrocarbons to produce light olefins and/or BTX have been discovered. The methods can be used to optimize heat integration and reduce the production cost for light olefins and/or BTX. As shown in FIG. 2, embodiments of the invention include method 200 for catalytic cracking. Method 200 may be implemented by system 100, as shown in FIG. 1.

According to embodiments of the invention, as shown in block 201, method 200 includes feeding feed stream 11 comprising hydrocarbons and catalyst into reaction riser 101. The hydrocarbons may include full range naphtha, light naphtha, or heavy naphtha. The catalyst may include regenerated catalyst or fresh catalyst. In embodiments of the invention, at block 201, feed stream 11 is fed into reaction riser 101 at a superficial gas velocity greater than 1.5 m/s, preferably greater than 1.5 to 7 m/s.

According to embodiments of the invention, as shown in block 202, method 200 includes subjecting, in reaction riser 101, the hydrocarbons of feed stream 11 under reaction conditions sufficient to crack the hydrocarbons and produce an effluent stream comprising cracked hydrocarbons, unreacted hydrocarbons, and spent catalyst. In embodiments of the invention, reaction conditions at block 202 include a reaction temperature in a range of 550 to 800° C. and all ranges and values there between including ranges of 550 to 600° C., 600 to 650° C., 650 to 700° C., 700 to 750° C., and 750 to 800° C. The reaction conditions at block 202 may further include a reaction pressure of 0.9 to 3 atm and all ranges and values there between including 0.9 to 1.2 atm, 1.2 to 1.5 atm, 1.5 to 1.8 atm, 1.8 to 2.1 atm, 2.1 to 2.4 atm, 2.4 to 2.7 atm, 2.7 to 3.0 atm. The reaction conditions at block 202 may further include a catalyst to oil ratio (weight based) in a range of 3 to 30 and all ranges and values there between including ranges of 3 to 6, 6 to 9, 9 to 12, 12 to 15, 15 to 18, 18 to 21, 21 to 24, 24 to 27, and 27 to 30. The reaction conditions at block 202 may further still include an average residence time in reaction riser 101 of 0.6 to 6 s and all ranges and values there between including ranges of 0.6 to 1.2 s, 1.2 to 1.8 s, 1.8 to 2.4 s, 2.4 to 3.0 s, 3.0 to 3.6 s, 3.6 to 4.2 s, 4.2 to 4.8 s, 4.8 to 5.4 s, and 5.4 to 6.0 s. In embodiments of the invention, the cracked hydrocarbons include light olefins and/or BTX.

According to embodiments of the invention, as shown in block 203, method 200 includes supplying heat from stripping zone 105 to reaction riser 101 to maintain the reaction temperature in a range of 550 to 800° C. In embodiments of the invention, the supplying at block 203 includes heating reaction riser 101 directly by internals 107. As an alternative or in addition to direct heating by internals 107, heating at block 203 may include heating reaction riser 101 via the stripping medium, which is heated by internals 107. In embodiments of the invention, internals 107 and/or the stripping medium are heated using flue gas, gas turbine, molten salt, any other heating media, or combinations thereof. In embodiments of the invention, the heating conditions (e.g., temperature, flow rate etc.) of internals 107 and/or stripping medium can be adjusted based on the heat required by reaction riser to maintain the reaction temperature.

According to embodiments of the invention, as shown in block 204, method 200 includes separating, in separation zone 102, the effluent stream from reaction riser 101 to produce (1) product stream 13 comprising cracked hydrocarbons and unreacted hydrocarbons, and (2) spent catalyst stream 14. In embodiments of the invention, product stream 13 comprises 20 to 45 wt. % light olefins and 4 to 10 wt. % BTX. Spent catalyst stream 14 comprises the spent catalyst and residual hydrocarbons adsorbed thereon.

According to embodiments of the invention, as shown in block 205, method 200 includes stripping, in stripping zone 105, the spent catalyst to remove at least some residual hydrocarbons adsorbed thereon and produce a stripped spent catalyst using the stripping medium. In embodiments of the invention, stripping at block 205 and supplying at block 203 are performed concurrently by flowing heated stripping medium through stripping zone 105. In embodiments of the invention, the stripping medium at block 205 is at a temperature of 500 to 700° C. At block 205, internals 107 may be heated to a temperature of 500 to 700° C. and all ranges and values there between including ranges of 500 to 510° C., 510 to 520° C., 520 to 530° C., 530 to 540° C., 540 to 550° C., 550 to 560° C., 560 to 570° C., 570 to 580° C., 580 to 590° C., 590 to 600° C., 600 to 610° C., 610 to 620° C., 620 to 630° C., 630 to 640° C., 640 to 650° C., 650 to 660° C., 660 to 670° C., 670 to 680° C., 680 to 690° C., and 690 to 700° C.

According to embodiments of the invention, as shown in block 206, method 200 includes regenerating, in catalyst regenerator 109, the spent catalyst to produce regenerated catalyst stream 15 comprising the regenerated catalyst and flue gas stream 16 comprising primarily flue gas. In embodiments of the invention, regenerating at block 206 is configured to remove coke formed on the spent catalyst and restore heat to regenerated catalyst. In embodiments of the invention, regenerating at block 206 is conducted at a regeneration temperature of 600 to 800° C. and all ranges and values there between including ranges of 600 to 610° C., 610 to 620° C., 620 to 630° C., 630 to 640° C., 640 to 650° C., 650 to 660° C., 660 to 670° C., 670 to 680° C., 680 to 690° C., and 690 to 700° C., 700 to 710° C., 710 to 720° C., 720 to 730° C., 730 to 740° C., 740 to 750° C., 750 to 760° C., 760 to 770° C., 770 to 780° C., 780 to 790° C., and 790 to 800° C. In embodiments of the invention, regenerating at block 206 is conducted in the presence of a regenerating gas comprising air and fuel. In embodiments of the invention, the regenerated catalyst produced at block 206 is at a temperature of 600 to 800° C. and all ranges and values there between including ranges of 600 to 610° C., 610 to 620° C., 620 to 630° C., 630 to 640° C., 640 to 650° C., 650 to 660° C., 660 to 670° C., 670 to 680° C., 680 to 690° C., and 690 to 700° C., 700 to 710° C., 710 to 720° C., 720 to 730° C., 730 to 740° C., 740 to 750° C., 750 to 760° C., 760 to 770° C., 770 to 780° C., 780 to 790° C., and 790 to 800° C. In embodiments of the invention, regenerated catalyst stream 15 is mixed with hydrocarbon feed to form feed stream 11.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

In the context of the present invention, at least the following 20 embodiments are described. Embodiment 1 is a fluidized catalytic cracking apparatus. The apparatus includes a reaction riser configured to receive a mixture containing a hydrocarbon feed and a cracking catalyst and crack the hydrocarbons to produce cracked hydrocarbons and a spent catalyst containing residual hydrocarbons adsorbed thereto. The apparatus also includes a stripping zone fluidly coupled to the reaction riser and encompassing at least a portion of the reaction riser, wherein the stripping zone includes a stripping medium inlet configured to receive a stripping medium, and a plurality of internals configured to (a) strip the residual hydrocarbons from the spent catalyst via the stripping medium and/or (b) provide heat to the reaction riser. Embodiment 2 is the fluidized catalytic cracking apparatus of embodiment 1, further including an outlet fluidly coupled to the stripping zone, configured to release stripped spent catalyst from the stripping zone, and a catalyst regenerator fluidly coupled to the outlet, the catalyst regenerator is configured to regenerate the spent catalyst to produce flue gas and a regenerated catalyst. Embodiment 3 is the fluidized catalytic cracking apparatus of embodiment 2, wherein the internals includes heating plates coupled to an internal wall of the stripping zone and/or heating plates submerged in the stripping zone. Embodiment 4 is the fluidized catalytic cracking apparatus of embodiment 3, wherein the stripping internals is configured to provide heat to the reaction riser by heating a heating medium in contact with the reaction riser. Embodiment 5 is the fluidized catalytic cracking apparatus of embodiment 4, wherein the heating medium is selected from a hot oil, the stripping medium, the flue gas produced by the catalyst regenerator, gas turbine, molten salts, etc., or combinations thereof. Embodiment 6 is the fluidized catalytic cracking apparatus of any of embodiments 3 to 5, wherein the stripping internals is configured to provide heat to the reaction riser by directly heating the reaction riser. Embodiment 7 is the fluidized catalytic cracking apparatus of any of embodiments 3 to 6, wherein the heating plates and/or the stripping medium is heated using the flue gas produced by the catalyst regenerator. Embodiment 8 is the fluidized catalytic cracking apparatus of any of embodiments 1 to 7, further including a separation zone fluidly coupled to the stripping zone, wherein the separation zone includes a cyclone system fluidly coupled to an outlet of the reaction riser, configured to separate an effluent stream from the reaction riser to form a product stream and the spent catalyst stream, and a reactor shell encompassing the cyclone system and the spent catalyst from the cyclone system. Embodiment 9 is the fluidized catalytic cracking apparatus of embodiment 8, wherein the reactor shell further encompasses at least a portion of the reaction riser. Embodiment 10 is the fluidized catalytic cracking apparatus of either of embodiments 8 or 9, wherein the cyclone system includes one or more cyclonic separators. Embodiment 11 is the fluidized catalytic cracking apparatus of any of embodiments 1 to 10, wherein the reaction riser is configured to maintain an isothermal profile. Embodiment 12 is the fluidized catalytic cracking apparatus of any of embodiments 1 to 11, wherein the catalyst contains ZSM-5, SAPO-34, dual function catalysts, or combinations thereof. Embodiment 13 is the fluidized catalytic cracking apparatus of any of embodiments 1 to 12, wherein the stripping medium includes steam, air, dry gas, or combinations thereof.

Embodiment 14 is a method of catalytically cracking hydrocarbons. The method includes flowing a feed stream containing hydrocarbons and a catalyst into the reaction riser of the fluidized catalytic cracking apparatus of any of embodiments 1 to 13. The method further includes subjecting, in the reaction riser, the feed stream under reaction conditions sufficient to crack the hydrocarbons and produce an effluent stream containing cracked hydrocarbons, unreacted hydrocarbons, and spent catalyst. The method still further includes supplying heat from the stripping zone to the reaction riser to maintain a reaction temperature in the reaction riser of 500 to 800° C. The method also includes separating, in the separation zone, the effluent stream to produce a product stream containing the cracked hydrocarbons and unreacted hydrocarbons, and a spent catalyst stream containing the spent catalyst. Embodiment 15 is the method of embodiment 14, further including stripping, in the stripping zone, the spent catalyst to produce a stripped spent catalyst using the stripping medium, and regenerating, in catalyst regenerator, the stripped spent catalyst to produce a regenerated catalyst and flue gas. Embodiment 16 is the method of embodiment 15, further including feeding the regenerated catalyst and the hydrocarbon stream into the reaction riser. Embodiment 17 is the method of either of embodiments 15 or 16, wherein the regenerating is conducted at a regenerating temperature of 600 to 800° C. Embodiment 18 is the method of any of embodiments 15 to 17, further including using the flue gas to provide heat to the internals of the stripping zone. Embodiment 19 is the method of any of embodiments 14 to 18, wherein the reaction conditions include a reaction temperature of 550 to 800° C., a reaction pressure of 0.9 to 3 atm, and a weight based catalyst to oil ratio of 3 to 30. Embodiment 20 is the method of any of embodiments 14 to 19, wherein the cracked hydrocarbons include light olefins and/or BTX.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A fluidized catalytic cracking apparatus comprising:
   a reaction riser configured to receive a mixture comprising a hydrocarbon feed and a cracking catalyst and crack the hydrocarbons to produce cracked hydrocarbons comprising light olefins and a spent catalyst comprising residual hydrocarbons adsorbed thereto;
   a stripping zone fluidly coupled to the reaction riser and encompassing at least a portion of the reaction riser, wherein the stripping zone comprises:
   a stripping medium inlet configured to receive a stripping medium;
   a plurality of internals configured to (a) strip the residual hydrocarbons from the spent catalyst via the stripping medium and/or (b) provide heat to the reaction riser;
   an outlet fluidly coupled to the stripping zone, configured to release stripped spent catalyst from the stripping zone; and
   a catalyst regenerator fluidly coupled to the outlet, wherein the catalyst regenerator is configured to regenerate the spent catalyst to produce flue gas and a regenerated catalyst;
   wherein the internals comprises heating plates coupled to 1) an internal wall of the stripping zone and/or 2) heating plates submerged in the stripping zone;
   wherein the stripping medium comprises steam, air, dry gas, or combinations thereof;
   wherein the stripping internals is configured to provide heat to the reaction riser by heating a heating medium in contact with the reaction riser; and
   wherein the heating medium is selected from a hot oil, the stripping medium, the flue gas produced by the catalyst regenerator, a gas turbine, a molten salt, or combinations thereof.

2. The fluidized catalytic cracking apparatus of claim 1, wherein the internals comprises heating plates coupled to an internal wall of the heating plates submerged in the stripping zone.

3. The fluidized catalytic cracking apparatus of claim 1, wherein the internals comprises heating plates coupled to an internal wall of the stripping zone and heating plates submerged in the stripping zone.

4. The fluidized catalytic cracking apparatus of claim 1, wherein the heating medium is the molten salts.

5. The fluidized catalytic cracking apparatus of claim 3, wherein the stripping internals is configured to provide heat to the reaction riser by directly heating the heating medium in contact with the reaction riser.

6. The fluidized catalytic cracking apparatus of claim 3, wherein the heating plates and/or the stripping medium is heated using the flue gas produced by the catalyst regenerator.

7. The fluidized catalytic cracking apparatus of claim 1, further comprising a separation zone fluidly coupled to the stripping zone, wherein the separation zone comprises:
   a cyclone system fluidly coupled to an outlet of the reaction riser, configured to separate an effluent stream from the reaction riser to form a product stream and the spent catalyst stream; and
   a reactor shell encompassing the cyclone system and the spent catalyst from the cyclone system.

8. The fluidized catalytic cracking apparatus of claim 7, wherein the reactor shell further encompasses at least a portion of the reaction riser.

9. The fluidized catalytic cracking apparatus of claim 7, wherein the cyclone system comprises one or more cyclonic separators.

10. The fluidized catalytic cracking apparatus of claim 1, wherein the reaction riser is configured to maintain an isothermal profile.

11. The fluidized catalytic cracking apparatus of claim 1, wherein the catalyst comprises at least one member selected from the group consisting of ZSM-5 and SAPO-34.

12. The fluidized catalytic cracking apparatus of claim 1, wherein the stripping medium comprises steam, air, dry gas, or combinations thereof.

13. A method of catalytically cracking hydrocarbons, the method comprising:
- flowing a feed stream comprising hydrocarbons and a catalyst into the reaction riser of the fluidized catalytic cracking apparatus of claim 1;
- subjecting, in the reaction riser, the feed stream under reaction conditions sufficient to crack the hydrocarbons and produce an effluent stream comprising cracked hydrocarbons, unreacted hydrocarbons, and spent catalyst;
- supplying heat from the stripping zone to the reaction riser to maintain a reaction temperature in the reaction riser of 500 to 800° C.;
- separating, in the separation zone, the effluent stream to produce a product stream comprising the cracked hydrocarbons and unreacted hydrocarbons, and a spent catalyst stream comprising the spent catalyst;
- stripping, in the stripping zone, the spent catalyst to produce a stripped spent catalyst using the stripping medium; and
- regenerating, in catalyst regenerator, the stripped spent catalyst to produce a regenerated catalyst and flue gas.

14. The method of claim 13, wherein the regenerating is conducted at a regenerating temperature of 800° C.

15. The method of claim 14, further comprising feeding the regenerated catalyst and the hydrocarbon stream into the reaction riser.

16. The method of claim 14, wherein the regenerating is conducted at a regenerating temperature of 650 to 800° C.

17. The method of claim 16, wherein the regenerating is conducted at a regenerating temperature of 700 to 800° C.

18. The method of claim 13, wherein the reaction conditions include a reaction temperature of 650 to 800° C., a reaction pressure of 0.9 to 3 atm, and a weight based catalyst to oil ratio of 3 to 30.

19. The method of claim 13, wherein the cracked hydrocarbons include light olefins and/or BTX.

* * * * *

UNITED STATES PATENT AND TRADEMARK OFFICE
CERTIFICATE OF CORRECTION

| | |
|---|---|
| PATENT NO. | : 12,233,405 B2 |
| APPLICATION NO. | : 17/630459 |
| DATED | : February 25, 2025 |
| INVENTOR(S) | : Talal Khaled Al-Shammari |

It is certified that error appears in the above-identified patent and that said Letters Patent is hereby corrected as shown below:

In the Claims

At Column 10, Claim number 4, Line number 35, delete "salts" and replace with --salt--.

Signed and Sealed this
Fifteenth Day of April, 2025

Coke Morgan Stewart
*Acting Director of the United States Patent and Trademark Office*